United States Patent [19]

Twardowski et al.

[11] Patent Number: 4,604,379

[45] Date of Patent: Aug. 5, 1986

[54] DIALYSIS SOLUTIONS CONTAINING CROSS-LINKED GELATIN

[75] Inventors: Zbylut J. Twardowski; Karl D. Nolph, both of Columbia, Mo.

[73] Assignee: Curators of the University of Missouri, Columbia, Mo.

[21] Appl. No.: 621,392

[22] Filed: Jun. 18, 1984

[51] Int. Cl.[4] ...................... C08L 89/04; C08L 89/06; C09H 7/00
[52] U.S. Cl. ........................................ 514/21; 530/354
[58] Field of Search ............................ 260/117; 514/21

[56] References Cited

U.S. PATENT DOCUMENTS 3,057,782 10/1962 Linder et al. .......................... 514/21
4,339,433 7/1982 Kartinos et al. ....................... 424/78

FOREIGN PATENT DOCUMENTS 546929 10/1957 Canada .

OTHER PUBLICATIONS

Publication entitled *Modified Gelatins as Plasma Substitutes;* Bibl. Haemat., No. 33 (Karger, Basel/New York 1969), pp. 55–125.

Primary Examiner—Howard E. Schain
Attorney, Agent, or Firm—Paul C. Flattery; Garrettson Ellis; Daniel D. Ryan

[57] ABSTRACT

Peritoneal dialysis solution may have an osmotic agent as a partial or complete substitute to the conventional dextrose. The osmotic agent is gelatin chemically cross-linked to suppress gelation.

6 Claims, No Drawings

DIALYSIS SOLUTIONS CONTAINING CROSS-LINKED GELATIN

TECHNICAL FIELD AND PRIOR ART

In Kartinos et al., U.S. Pat. No. 4,339,433, polymeric osmotic agents are proposed for use in peritoneal dialysis solution as an alternative to dextrose.

The dextrose in the conventional peritoneal dialysis solution is provided to cause ultrafiltration to take place by osmotic principles from the blood through the peritoneum of a patient into the dialysis solution in the peritoneal cavity, to cause removal of water from the dialysis patient.

While dextrose is an effective material and virtually the only osmotic agent used in commercially available peritoneal dialysis solution at the present time, it has certain drawbacks. First, a great deal of dextrose passes through the peritoneum into the patient's bloodstream during peritoneal dialysis. While this does provide carbohydrate nutrition, difficulties can be encountered by some groups of patients, particularly diabetic patients and certain other patients who have a tendency to develop high serum lipids in the presence of such large amounts of glucose.

Since end stage renal disease patients, whose lives are being maintained by dialysis, must undergo a certain amount of ultrafiltration every day to remove water from their circulatory systems, it is not practical simply to reduce the amount of dextrose in the peritoneal dialysis solution. The ultrafiltration that it provides is mandatory in most cases.

Accordingly, in the Kartinos patent cited above, alternate materials to dextrose were proposed; specifically, a predominently sodium salt of a reaction product of gelatin and a dicarboxylic acid or its anhydride, to produce a polyanionic protein material having pendant carboxyl groups. The gelatin material makes use of the polyanionic characteristic provided by the pendant carboxyl groups on the material to provide osmotic characteristics to the solution.

In accordance with this invention, new gelatin-based osmotic agents for peritoneal dialysis solutions are proposed. Some of these agents appear to have reduced immunogenicity, rendering them highly desirable for use in peritoneal dialysis solution. The new osmotic agents of this invention, being of relatively high molecular weight, pass only slowly through the peritoneum with the result that peritoneal dialysis solutions contaning them can retain their capability for ultrafiltration over many hours of dwell in the peritoneal cavity, a period of time which is substantially longer than the corresponding time for glucose-based peritoneal dialysis solutions.

DESCRIPTION OF THE INVENTION

In this invention a peritoneal dialysis solution is provided having an osmolarity which is capable of permitting safe diffusion exchange across the peritoneum after infusion into the peritoneal cavity of the patient. In accordance with this invention, the peritoneal dialysis solution contains gelatin which is cross-linked to suppress gelatin. The peritoneal dialysis solution is at a physiological pH to cause such gelatin to assume polyanionic characteristics, there being sufficient physiological cations present, predominently sodium, to permit the anionic gelatin to be at such pH. The gelatin is typically essentially free of synthetically added pendant ionizable groups such as carboxyl groups.

It is generally desirable for the peritoneal dialysis solution of this invention to be of at least pH 6 with a typical upper limit being pH 7.5 or 8.0. However, the pH may be as low as 5.2 or 5.5, as may be necessary when dextrose is included in the solution. Gelatins which are cross-linked in a manner to suppress gelation are known and commercially available. For example, Haemaccel is the trademark of a product of Farbwerke Hoechst A. G. of Frankfurt-Hoechst, West Germany. It is the reaction product of gelatin with an aliphatic diisocyanate, for example examethylene diisocyanate, having a mean molecular weight of 30,000–35,000. For further description, see the article entitled "Chemistry and Physicochemical Characterizations of Gelatin Plasma Substitutes" by H. H. Schöne from *Modified Gelatins as Plasma Substitutes;* Bibl. haemat., No. 33, pp. 78–80, (Karger, Basel/New York, 1969). The material has been conventionally used as a blood expander for intravenous administration. Another material which may be used in this invention is sold by Biotest A. G. under the trademark Gelifundol. It is a form of gelatin which is cross-linked with dialdehyde glyoxal.

It has been found that such cross-linked gelatins substantially lack the capability to gel at room temperature and above. They tend to have an isoelectric point at a pH below 5. Accordingly, when the pH is above 5 and preferably 6 to 7.5, the cross-linked gelatins, and particularly those described above, assume an anionic characteristic. Sufficient physiological cations will be provided to the dialysis solution to cause the anionic gelatin to assume a salt form. The primary cation used is typically sodium, although other physiological cations such as potassium, calcium, and/or magnesium may be present as desired along with the sodium. The selection and concentrations of salts for providing said cations is a routine matter for those skilled in the art.

As a result of this, the high molecular weight gelatin exhibits increased osmotic effect because of the sodium and other cations that are attracted to the anionic gelatin, while at the same time gelation of the material is suppressed. As a result of this, when placed in the peritoneal cavity as part of the peritoneal dialysis solution, the large gelatin polyanions and their associated cations exhibit a relatively long lasting osmotic effect since the gelatin molecules pass only very slowly through the peritoneum into the blood stream of the patient. Accordingly, the associated cations are likewise prevented from migration by their electrostatic attraction to the gelatin.

The resulting long-lasting osmotic effect permits ultrafiltration to take place throughout most or all of the dwell period that the peritoneal dialysis solution resides in the peritoneal cavity of the patient, typically a period of 4 to 10 hours. As a result of this, reduced dextrose concentrations can be used in the peritoneal dialysis solution, or not at all in some circumstances. However it may be desired for dextrose to be present in reduced quantities to provide an initial surge of ultrafiltration, and also to provide carbohydrate nutrition to the patient.

Other physiological materials, as may be desired, may be placed in the peritoneal dialysis solution of this invention along with the cross-linked gelatin and appropriate electrolyte salts such as sodium chloride, magnesium chloride, sodium acetate, sodium lactate, sodium bicarbonate or potassium chloride. As stated above, dextrose may be added to the solution of this invention, and any other known additive for peritoneal dialysis solution may be present as well.

EXAMPLE 1

Nonuremic Sprague Dawley rats weighing 310–390 g. were anesthesized by injection of pentabarbitol sodium. A silicone catheter without cuff was inserted into the peritoneal cavity through a midline incision in the abdomen below the sternum. The interior end of the catheter was positioned in the inferior right quadrant of the peritoneal cavity.

Peritoneal dialysis solution was prewarmed to 37° C., and 20 ml. was administered to each rat over 1 minute of time. Thereafter, the peritoneal dialysis solution was immediately drained in order to determine the undrainable peritoneal solution volume retained in the peritoneal cavity. Then the same aliquot of solution that was drained was reinfused.

Thereafter, at hourly intervals, the peritoneal dialysis solution was drained again, and the volume measured, followed by reinfusion of the same volume of solution until the end of the experiment.

Ultrafiltration volumes as recorded here are the undrainable volume plus the apparent ultrafiltration volumes at each dwell time.

A. A first hemodialysis solution used in the above experiment was of the following formulation:

| Hemaccel ® cross-linked gelatin-5.5 weight percent | |
|---|---|
| Sodium | 147.6 meq./l. |
| Potassium | 4.3 meq./l. |
| Magnesium | 0.59 meq./l. |
| Calcium | 4.79 meq./l. |
| Chloride | 108 meq./l. |
| Osmolality of this solution was 290 milliosmols/kilogram. | |

The diffusible free electrolytes of the above solution as determined by the Gibbs Donan distribution ratio were as follows:

| Sodium | 141.1 meq./l. |
|---|---|
| Potassium | 4.1 meq./l. |
| Magnesium | 0.146 meq./l. |
| Calcium | 3.54 meq./l. |
| Chloride | 111 meq./l. |
| Osmolality 272 milliosmols/kilogram. | |

The experimental results with respect to ultrafiltration for the above solution were as follows:

After 1 hr. of dwell, ultrafiltration was 2.9 ml.±0.4 ml.

After 3 hrs. ultrafiltration was 6.5 ml.±0.5 ml.

After 4 hrs. of dwell, ultrafiltration was 7 ml.±0.5 ml.

After 6 hrs. of dwell, ultrafiltration was 6.7 ml.±0.5 ml.

The above data were determined from 4 rats.

B. The above described experiment was repeated using peritoneal dialysis solution made of the following formulation:

| Hemaccel ® cross-linked gelatin-10 weight percent | |
|---|---|
| Sodium | 149.3 meq./liter |
| Potassium | 4.5 meq./liter |
| Magnesium | 0.64 meq./liter |
| Calcium | 5.23 meq./liter |
| Chloride | 105 meq./liter |
| Osmolality 298 milliosmols/kilogram. | |

The diffusible electrolyte concentrations in accordance with the Gibbs-Donan distribution ratio were substantially identical to the diffusable electrolytes of the previous peritoneal dialysis solution formulation.

Ultrafiltration data from 4 rats tested were as follows:

At 1 hr. of dwell, ultrafiltration was 2.0 ml.±0.2 ml.

At 3 hrs. of dwell, ultrafiltration was 4.6 ml.±0.9 ml.

At 4 hrs. of dwell, ultrafiltration was 8.6 ml.±1.0 ml.

At 5 hrs. of dwell, ultrafiltration was 10.6 ml.±0.9 ml.

At 6 hrs. of dwell, ultrafiltration was 11.6 ml.±0.9 ml.

It can be seen that the peritoneal dialysis solutions of this invention exhibit long-term ultrafiltration permitting a relatively steady ultrafiltration over periods of time which may approximate the entire dwell period of a peritoneal dialysis procedure. This can be accomplished in the absence of dextrose, if desired, so that peritoneal dialysis solutions of this invention may exhibit great flexibility of use and benefit to patients who have difficulty tolerating the dextrose contents of the presently conventional peritoneal dialysis solutions.

The above has been offered for illustrative purposes only and is not intended to limit the scope of the invention of this application, which is as defined in the claims below.

What is claimed is:

1. A peritoneal dialysis solution comprising
   an osmotic agent operative, when said solution is present in the peritoneal cavity, to induce and sustain the ultrafiltration of water from the blood into said solution through the peritoneum, said osmotic agent comprising gelatin which is chemically cross-linked to suppress gelatin and which has an isoelectric point at a pH below about 5, said cross-linked gelatin being essentially free of synthetically added, pendant ionizable groups, and
   a quantity of physiological cations present to maintain said solution at a pH above about 5 to create a normally anionic charge on said cross-linked gelatin and to cause said cross-linked gelatin to assume a salt form.

2. The peritoneal dialysis solution of claim 1 in which said physiological cations are selected from the group consisting of sodium, magnesium, potassium, and calcium.

3. The peritoneal dialysis solution of claim 1 in which said cross-linked gelatin is the reaction product of gelatin and an aliphatic diisocyanate.

4. The peritoneal dialysis solution of claim 1 in which said cross-linked gelatin is the reaction product of gelatin and dialdehyde glyoxal.

5. The peritoneal dialysis solution of claim 1 which has a pH of 6.0–7.5.

6. The peritoneal dialysis solution of claim 1 which contains dextrose as an added osmotic agent.

* * * * *